(12) United States Patent
Mercola

(10) Patent No.: US 6,579,856 B2
(45) Date of Patent: Jun. 17, 2003

(54) INHIBITION OF STRESS ACTIVATED PROTEIN KINASE (SAPK) PATHWAY AND SENSITIZATION OF CELLS TO CANCER THERAPIES

(76) Inventor: Daniel Mercola, P.O. Box 3752, Rancho Santa Fe, CA (US) 92067

( * ) Notice: Subject to any disclaimer, the term of this patent is extended or adjusted under 35 U.S.C. 154(b) by 0 days.

(21) Appl. No.: 09/955,406

(22) Filed: Sep. 12, 2001

(65) Prior Publication Data

US 2002/0107218 A1 Aug. 8, 2002

Related U.S. Application Data

(62) Division of application No. 09/265,350, filed on Mar. 9, 1999, which is a continuation of application No. 08/864,603, filed on May 28, 1997, now abandoned.

(51) Int. Cl.$^7$ ................................................ A61K 48/00
(52) U.S. Cl. ........................ 514/44; 435/375; 435/377
(58) Field of Search ........................... 514/44; 435/375, 435/377, 455

(56) References Cited

PUBLICATIONS

Potapova, et al., *Proc. Amer. Assoc. Cancer Res.*, 38:139 Abst. 930 (1997).
Verma et al., *Nature*, 389:239–242 (1997).
Harris et al., *TIG*, 12(10):400–405 (1996).
Crystal, R. *Science*, 270:404–410 (1995).
Anderson, W. *Nature*, 392:25–30 (1998).
Bost et al., *The J. of Biol. Chem.*, 272(52):33422–33429 (1997).

*Primary Examiner*—Sean McGarry
(74) *Attorney, Agent, or Firm*—David B. Waller & Associates

(57) ABSTRACT

The present invention provides compositions that can be administered to an individual and inhibit a stress activated protein kinase pathway. The invention also provides methods of increasing the sensitivity of cancer cells to a cancer therapy by contacting the cancer cells with a stress activated protein kinase pathway inhibitor. The invention further provides methods of reducing the severity of a cancer in a patient by administering to the patient a stress activated protein kinase pathway inhibitor and treating the patient with a conventional cancer therapy.

8 Claims, No Drawings

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (xi) SEQUENCE DESCRIPTION: SEQ ID NO: 1:

ACACATTTCA TAAGAACTAG                    20

(2) INFORMATION FOR SEQ ID NO: 2:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (xi) SEQUENCE DESCRIPTION: SEQ ID NO: 2:

TCATGAAGTT AGTGCACGCT                    20

(2) INFORMATION FOR SEQ ID NO: 3:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (xi) SEQUENCE DESCRIPTION: SEQ ID NO: 3:

TGGGATTACA CGTGTGAACC AACC               24

(2) INFORMATION FOR SEQ ID NO: 4:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (xi) SEQUENCE DESCRIPTION: SEQ ID NO: 4:

GATCCACAGT CTGCCTGAGT CACT               24

(2) INFORMATION FOR SEQ ID NO: 5:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (xi) SEQUENCE DESCRIPTION: SEQ ID NO: 5:

CCTAGAAAGC ACATGGAGAG CTAG               24

INHIBITION OF STRESS ACTIVATED PROTEIN KINASE (SAPK) PATHWAY AND SENSITIZATION OF CELLS TO CANCER THERAPIES

CROSS-REFERENCE TO RELATED APPLICATIONS

This application is a divisional of patent application Ser. No. 09/265,350 filed Mar. 9, 1999 which is a continuation of patent application Ser. No. 08/864,603 filed May 28, 1997 now abandoned.

This invention was made with government support under CA 63783 awarded by the National Cancer Institute. The government has certain rights in the invention.

BACKGROUND OF THE INVENTION

Field of the Invention

The present invention relates generally to molecular medicine and cancer therapy and more specifically to compositions that inhibit the stress activated protein kinase pathway and methods of using such compositions to sensitize cancer cells to a cancer therapy.

Background Information

In renewing tissues such as bone marrow, the intestine and the skin, a steady state is maintained between the rate of cell growth and the rate of cell death. In particular, the rate of cell death in renewing tissue occurs through programmed cell death pathways and are characterized by the process of apoptosis. Disruption of this steady state often is associated with the development of cancer. For example, where the rate of programmed cell death is lower than normal, an increased number of cells occurs in a tissue, resulting in the formation of a tumor.

Cancer cells are characterized by an ability to proliferate indefinitely and to invade into normal tissue surrounding the tumor. In addition, many types of cancer cells can metastasize throughout the body such that the tumor is disseminated in the cancer patient.

Conventional methods for treating cancer have increased the survival and quality of life of cancer patients. Such conventional methods include surgery, radiotherapy and chemotherapy. In addition, bone marrow transplantation is becoming useful in treating patients with certain types of cancers.

Surgery generally is the first choice for treating patients having a tumor that is localized to a specific area of the human body. Tumor excision is quick and quite effective, accounting for the majority of cures. However, surgery has several disadvantages. One major obstacle to this form of treatment occurs when the tumor is in an inoperable location such that resection of the tumor is not possible. In addition, the cancer already may have spread to other parts of the body, but is not yet detectable at the time of surgery. While surgical removal of the localized tumor can improve the quality of the patient's life, the cancer is destined to recur in the other locations. Similarly, even when a tumor is localized and has not yet spread, failure to remove all of the cancer cells can result in recurrence of the tumor. Finally, surgery is, by nature, an invasive procedure and can cause loss of function of a normal tissue or organ or affect the patient's appearance.

Radiotherapy often is used in combination with, or as an alternative, to surgery. Radiation primarily causes damage to the tumor cell DNA, thus inducing apoptosis and death of the cells. Of course, normal cells in the radiation field also are damaged, but normal cells generally have a greater ability than cancer cells to recover from radiation damage and, therefore, a therapeutic benefit can be obtained. However, radiation therapy, like surgery, is a localized treatment and suffers from the same inadequacies, for example, failure to kill tumor cells that are outside of the treatment field, particularly metastatic lesions. In addition, radiation damage occurs to particularly susceptible tissues such as bone marrow, skin and intestine, thus causing patient morbidity.

In contrast to surgery and radiotherapy, chemotherapy provides a systemic method of treating cancer. Chemotherapy utilizes various classes of chemotherapeutic agents that have different modes of action. For example, antimetabolite chemotherapeutic agents generally share structural similarities with normal cellular components and exert their toxic effect by inhibiting a normal cellular process. For example, methotrexate is a chemical analogue of folic acid, which is a vitamin required for DNA synthesis. Methotrexate functions by competing with folic acid for binding to an enzyme normally involved in the conversion of folic acid into adenine and guanine, which are two building blocks of DNA. As a result of the competition, methotrexate prevents cells from dividing by inhibiting their ability to synthesize DNA.

Other chemotherapeutic agents, such as topoisomerase analogs or inhibitors and alkylating agents, also function by disrupting normal DNA synthesis in cells, resulting in death of the cells. Since tumor cells generally divide more rapidly than normal tissues, tumor cells are somewhat preferentially killed by such chemotherapeutic agents. However, as discussed above, cells such as bone marrow cells, intestinal epithelial cells and skin cells also are rapidly dividing and, therefore, susceptible to the toxic effects of such chemotherapeutic agents. In fact, it is the toxicity to normal cells that generally limits the dose of chemotherapeutic agent that can be administered to a patient. In addition, tumor cells have a propensity to acquire resistance to certain chemotherapeutic agents, further limiting the usefulness of such agents for treating cancer.

More recently, biochemical agents that are expressed normally in individuals and act as natural defense agents or as agents that induce natural immunity against diseased cells have been used as cancer therapeutic agents. In particular, the cytokines are a class of naturally occurring biochemicals that are involved in stimulation and activation of the immune response system. Such cytokines, including, for example, the interferons and interleukins can kill cells directly and provide the additional advantage that they can stimulate the patient's immune response. However, the normal expression of such biochemicals in the body is tightly regulated and the usefulness of agents is limited by the toxic effects that occur when higher than physiological amounts of these agents are administered to an individual.

In order to improve the therapeutic advantage of the various conventional cancer therapeutic modalities, the therapies often are used in combination. Thus, as toxicity to normal cells or tissues begins to occur due to the use of one modality, that modality is terminated and an second treatment using a different type of modality is initiated. Such first and second modalities can be, for example, surgery or radiotherapy, followed by chemotherapy, or a first type of chemotherapy followed by a second type of chemotherapy or a biochemical agent therapy.

In addition, a therapeutic advantage can be obtained by combining a therapeutic modality with treatment using an agent that modifies the effectiveness of the modality to a greater extent against cancer cells than normal cells. Such chemical modifiers generally are not toxic at the doses used, but act to modify or enhance the responsiveness of cancer cells to a conventional therapy. The effectiveness of a such chemical modifiers to sensitize tumor cells to a cytotoxic therapy generally is expressed as the sensitizer enhancement ratio, which is a ratio of the dose of a therapy required to produce a defined level of killing in the absence of the sensitizer to the dose required to produce the same level of cell killing in the presence of the sensitizer.

The use of chemical sensitizers is exemplified by the use of oxygen mimetics to increase the sensitivity of tumor cells to radiotherapy. Generally, the cancer cells forming a tumor grow faster than the cells that produce blood vessels in the tumor. As a result, as the tumor increases in size, it develops regions that are relatively deficient in oxygen. Such hypoxic tumor cells are relatively resistant to radiation damage and, therefore, limit the effectiveness of radiotherapy. However, chemical sensitizers have been developed that act as oxygen mimetics. The administration of such sensitizers to a cancer patient increases the "oxygenation" of the otherwise hypoxic tumor cells, thus rendering them more sensitive to a given dose of radiation. Since normal tissue generally is normally oxygenated, the use of such chemical sensitizers essentially has no effect on the normal cells. Of course, as discussed above, the use of radiotherapy nevertheless remains limited to treatment of patients having relatively localized tumors. Thus, while methods for treating cancer continue to improve, a need exists for compositions and methods that can generally increase the effectiveness of the variety of conventional cancer therapies currently available. The present invention satisfies this need and provides additional advantages.

SUMMARY OF THE INVENTION

The present invention provides compositions that inhibit a stress activated protein kinase (SAPK) pathway and are suitable for administration to an individual. For example, the invention provides compositions containing an antisense SAPK1, SAPK2 or SAPK3 nucleic acid molecule and a carrier, such that the composition is acceptable for administration to a human individual.

The invention also provides methods of increasing the sensitivity of cancer cells to a cancer therapeutic modality by inhibiting an SAPK in the cells. For example, the invention provides a method of increasing the sensitivity of cancer cells to a cancer therapeutic modality by expressing an antisense SAPK1, SAPK2 or SAPK3 nucleic acid molecule in the cells, wherein the antisense molecule inhibits the SAPK. The invention further provides methods of reducing the severity of a cancer in a patient by administering to the patient an SAPK pathway inhibitor. In addition, the patient can be treated with a conventional cancer therapy.

DETAILED DESCRIPTION OF THE INVENTION

The present invention provides compositions that inhibit a stress activated protein kinase (SAPK) pathway and are suitable for administration to an individual. The SAPK's (also called "jun N-terminal kinases" or "JNK's") are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. As disclosed herein, agents that inhibit SAPK activity in a cell prevent DNA repair and sensitize the cell to those cancer therapeutic modalities that act by inducing DNA damage.

Various cancer therapeutic modalities act by causing damage to DNA in the cancer cells or by adversely affecting DNA synthesis or replication in the cells and inducing apoptosis and cell death. Such genotoxic cancer therapeutic modalities include, for example, ionizing radiation; chemical agents that crosslink or otherwise directly damage DNA including cis-platinum and alkylating agents such as N-methyl-N'-nitro-N-nitroso-guanidine (MNNG) and methylmethanesulphonate (MMS); and agents that interfere with DNA synthesis including DNA chain terminating agents such as 1-β-arabinofuranosylcytosine (AraC), topoisomerase inhibitors such as camptothecin, and nucleoside analogs or precursors of such analogs such as methotrexate (MTX) and 5-flurouracil (5-FU).

The various cancer therapeutic modalities discussed above act by directly damaging DNA or by inhibiting DNA synthesis, thereby inducing apoptosis and death of the cancer cells. In addition, the SAPK pathway is involved in the mitogenic response of certain cells, including cancer cells. For example, human A549 tumor cells, which express an EGF receptor on their cell surface, respond mitogenically to EGF. However, the mitogenic response, but not basal growth, is inhibited when the SAPK pathway is inhibited by expressing a dominant negative c-jun mutant in the cells. Thus, in addition to sensitizing tumor cells to a cancer therapeutic modality, inhibition of the SAPK pathway also can block mitogenesis of tumor cells, for example, in response to an autocrine growth factor, thereby providing a therapeutic advantage to an individual treated with a cancer therapeutic modality. It should be recognized, however, that a SAPK inhibitory agent as disclosed herein can be useful, alone, for inhibiting proliferation of cancer cells and, therefore, for reducing the severity of a cancer in an individual.

For purposes of the present invention, the term "cancer therapeutic modality," unless specifically indicated otherwise, is used herein to mean those agents that induce DNA damage or inhibit DNA synthesis and induce apoptosis of a cell or that inhibit cell proliferation. It should be recognized that DNA damage or the inhibition of DNA synthesis can be caused directly by a cancer therapeutic modality, for example, as occurs due to alkylating agents, or can be caused indirectly, for example, by inhibiting or otherwise interfering with DNA synthesis or, as with radiation, by inducing the formation of free radicals, which damage DNA.

The SAPK pathway is activated in response to genotoxic agents such as ultraviolet radiation and various cancer therapeutic modalities (see, for example, Derijard et al., *Cell* 76:1025–1037 (1994); Adler et al., *J. Biol. Chem.* 270:26071–26077 (1995); van Dam et al., *EMBO J.* 14:1798–1811 (1995); Kharabanda et al., *Proc. Natl. Acad, Sci., USA* 93:6898–6901 (1996)). SAPK (JNK) phosphorylates c-jun at serine residues 63 and 73 (Smeal et al., *Nature* 354:494–496 (1991)). In turn, working backwards from c-jun activation in the SAPK pathway, SAPK is activated by phosphorylation of a SAPK kinase (SAPKK; JNKK), which, itself, is activated by phosphorylation of a SAPKK kinase (SAPKKK; JNKKK; also called MEKK1 and referred to herein as "MEKK1;" GenBank Accession No. U29671, which is incorporated herein by reference; see, also, U.S. Pat. No. 5,405,941, which is incorporated herein by reference). Additional steps of the pathway precede the activation of MEKK1 (Liu et al., Cell 87:565–576 (1996)) and, as discussed below, MEKK1 also acts as a branch point for a second pathway.

Various SAPK's, including SAPK1 (JNK; SAPK1α1; GenBank Accession No. 226318; see, also, U.S. Pat. No. 5,534,426, which is incorporated herein by reference), SAPK2 (SAPK2α1; U34821) and SAPK3 (SAPK3α1; U34820), and related isozymes, SAPK1α2 (U34822), SAPK1β1 (U35004), SAPK1β2 (U35005), SAPK2β1 (U35002), SAPK2β2 (U35003) and SAPK3α2 (U34819), each of which is incorporated herein by reference, have been described (see Gupta et al., *EMBO J*. 15:2760–2770 (1996)). Activation of one or more SAPK's in a cell is associated with the induction of expression of various genes involved in DNA repair and cell survival following a stress, including the genes encoding c-jun (Chu et al., *Mol. Endocrinol*. 8:59 (1994)), p21(Waf1/Cip1) (El-Deiry et al., *Cancer Res*. 55:2910 (1995)), ATF2, ATF3 (Gately et al., *Brit. J. Cancer* 70:1102 (1994)), PCNA (Huang et al., *Mol. Cell. Biol*. 14:4233 (1994)), cyclin-A, cyclin-D1 (Herbert et al., *Oncogene* 9:1295 (1994)), cyclin-G and GADD153 (Luethy and Holbrook, *Cancer Res*. 54:1902S (1994); Gately et al., supra, 1994).

The SAPK pathway likely is active in cancer cells. For example, tumors provide a stress-inducing environment for the cancer cells due to hypoxia in regions distant from blood vessels and to exposure to cell breakdown products and inflammatory signals that occur in regions of necrosis. In this regard, DNA damage commonly is observed in cancer cells. In addition, the SAPK pathway leads to activation of various transcription factors, some of which are involved in cell growth and proliferation. Thus, increased SAPK activity can be present in cancer cells that are proliferating relatively rapidly. Accordingly, a composition that inhibits a SAPK pathway as disclosed herein can be useful to inhibit proliferation, growth or DNA repair in cancer cells, thereby increasing the likelihood that cancer cells containing such damage will die. Furthermore, particular cancer cells can express one or more specific SAPK isozymes or unique SAPK kinases or MEKK1 kinases. Thus, the skilled artisan will recognize that the specific SAPK, SAPK kinase or MEKK1 isozyme or isozymes expressed in specific cancer cells can be selectively inhibited using a composition of the invention that is specific for the isozyme. Antisense molecules or ribozymes, for example, can exhibit such selectivity.

In addition to the prevalence of DNA damage that occurs in cancer cells in a tumor, administration of a cancer therapeutic modality to an individual results in DNA damage to the cancer cells, as well as to normal cells, and induces the SAPK pathway. Depending on the level of DNA damage, either the cells repair the damage and survive or the cells die. In general, the amount of a cancer therapeutic modality that an individual receives is limited by toxicity to normal tissues. The present invention provides a therapeutic benefit to an individual receiving a cancer therapeutic modality because the amount of the modality that is administered to the individual can be reduced due to inhibition of SAPK activity and, therefore, failure of the damaged cells to repair DNA damage due to the modality.

The present invention can provide a therapeutic benefit to an individual receiving a cancer therapeutic modality in various ways. For example, the amount of the modality that must be administered to the individual can be reduced due to inhibition of DNA repair due to inhibition of SAPK activity. Thus, where a side effect due to the modality is due to an intrinsic sensitivity of the particular patient, the sensitivity can be ameliorated due to administration of a lesser amount of cancer therapeutic modality. In addition, it is recognized that SAPK proteins constitute a family of at least three SAPK proteins, as well as isozymes of each SAPK protein, indicating that various cells, including cancer cells, likely differentially express one or more particular SAPK proteins. Thus, a method of the invention can be practiced so as to specifically inhibit the activity of the SAPK or SAPK proteins expressed by the cancer cells, thus inhibiting DNA repair in those cells but not in other cells such as normal cells expressing different SAPK protein. The identification of SAPK proteins expressed in cancer cells of an individual to be treated can be determined, for example, by western blot analysis using antibodies specific for SAPK isozymes. Furthermore, certain cancer cells can express SAPK constitutively, resulting in a greater than normal steady-state SAPK activity. For example, whereas normal lung cells do not express SAPK, non-small cell lung carcinoma cells either exhibit constitutive SAPK activity or SAPK activity can be induced by exposure to ultraviolet irradiation, which induces the SAPK pathway. These observations indicate that such cancer cells have an enhanced capacity for DNA repair and, therefore, an increased resistance to a cancer therepeutic modality. Thus, inhibition of SAPK activity in such cells can preferentially sensitize the cancer cells to a cancer therapeutic modality.

In one embodiment of the invention, SAPK activity is directly inhibited in a cancer cell, thereby decreasing the ability of the cell to repair DNA damage caused by a cancer therapeutic modality and increasing the sensitivity of the cancer cell to the cancer therapeutic modality. As used herein, the term "SAPK activity" means the ability of a SAPK to phosphorylate its substrate such as the ability of SAPK1 to phosphorylate c-jun on serine-63 and serine-73, or to mediate phosphorylation-dependent activation of transcription, specifically that mediated by phosphorylation of serine-63 and serine-73. In this regard, it is recognized that c-jun associates with a Fos family member to form heterodimers that bind to specific promoters and modestly increase the level of gene transcription. If, however, serine-63 and serine-73 of c-jun are phosphorylated by SAPK, a high level of transcriptional activity occurs. Thus, a SAPK mediates phosphorylation-dependent activation of transcription. Methods for identifying SAPK activity are well known in the art (see, for example, Hibi et al., *Genes Devel*. 7:2135–2148 (1993), which is incorporated herein by reference).

The present invention provides compositions containing a SAPK inhibitory agent that directly inhibits the activity of a SAPK in a cell. Such an agent can be an antisense SAPK nucleic acid molecule or a SAPK ribozyme, which directly inhibit SAPK activity by preventing the expression of the SAPK in the cell; can be a dominant negative mutant, such as a nonphosphorylatable form of c-jun, which directly inhibits SAPK activity by preventing SAPK from phosphorylating normal c-jun in a cell; or can be an small molecule such as a drug, which directly alters the interaction of proteins in the SAPK pathway. Although no mechanism of action is proposed as to how a dominant negative c-jun mutant can inhibit a SAPK pathway and, therefore, SAPK activity, the mutant c-jun may bind to and competitively inhibit the activity of SAPK in all its forms, or the mutant c-jun may form heterodimers with Fos family members or with ATF2, but lack the ability to participate in phosphorylation-dependent activation of transcription due to the inability of the mutant c-jun to be phosphorylated. The inhibition of SAPK activity can be determined, for example, by measuring the phosphorylation of a substrate such as c-jun (Hibi et al., supra, 1993) or, where SAPK activity is inhibited using an antisense SAPK nucleic acid, by performing an immunoassay using anti-SAPK antibodies, which are commercially available (Santa Cruz Biotechnology, Inc.; Santa Cruz Calif.).

As discussed above, activation of MEKK1 lead to c-jun activation. In addition, MEKK1 represents a branch point for a second pathway that leads to activation of the inhibitor of NF-KB (IKB) and activation of the NF-KB transcription factor (Lee et al., Cell 88:213–222 (1997)). Activation of NF-KB suppresses apoptosis (Beg et al., Science 274:782–789 (1996); van Antwerp et al., Science 274:787–789 (1996); Liu et al., supra, 1996) and it has been proposed that inhibiting NF-KB can potential killing of tumor cells by chemotherapeutic agents (Wang et al., Science 274:784–787 (1996)). Accordingly, in a second embodiment of the invention, SAPK activity in a cell is inhibited indirectly by inhibiting the activity of MEKK1 in the cell.

By inhibiting MEKK1 activity in a cancer cell, SAPKK is not activated and, therefore, does not activate SAPK, thus increasing the sensitivity of the cell to a cancer therapeutic modality, as discussed above. As an additional advantage, the inhibition of MEKK1 activity results in the inhibition of IKB activity and, therefore, NF-KB activation, thus increasing the sensitivity of the cells to apoptosis. Thus, the invention provides a composition comprising a SAPK inhibitory agent that inhibits MEKK1 activity, for example, an antisense MEKK1 nucleic acid molecule.

For example, the invention provides compositions containing an antisense SAPK1, SAPK2 or SAPK3 nucleic acid molecule and a carrier that is acceptable for administration to a human individual. An antisense nucleic molecule useful in the invention is a polymer of about twelve to fifty nucleotides, generally about fifteen to thirty-five nucleotides and usually about twenty to twenty-five nucleotides, which are linked by a covalent bond, such as a phosphodiester bond, a thioester bond, or any of various other bonds known in the art as useful and effective for linking nucleotides.

A nucleic acid molecule encoding an antisense SAPK isozyme or antisense MEKK1 useful in the invention, or a ribozyme or a dominant negative mutant, as discussed below, can be expressed from a vector, which is introduced into a cell in which it is desired to express the antisense molecule or ribozyme or dominant negative mutant. Antisense SAPK or MEKK1 nucleic acid molecules or SAPK or MEKK1 ribozymes also conveniently can be chemically synthesized. For example, an antisense SAPK1 having the sequence 5'-ACACATTTCATAAGAACTAG-3' (SEQ ID NO: 1) or an antisense SAPK2 having the sequence 5'-TCATGAAGTTAGTGCACGCT-3'(SEQ ID NO: 2) can be chemically synthesized (see, also, Seimiya et al., *J. Biol. Chem.* 272:4631–4636 (1997)).

An advantage of expressing the antisense molecule or ribozyme or dominant negative mutant in the desired cells is that it can be expressed at a relatively high level, increasing the ability of the molecule to inhibit SAPK activity. An expression vector expressing, for example, an antisense SAPK or MEKK1 nucleic acid molecule can be introduced into cells using well known transfection methods (see, for example, Sambrook et al., *Molecular Cloning: A laboratory manual* (Cold Spring Harbor Laboratory Press 1989); Ausubel et al., *Current Protocols in Molecular Biology* (Green Publ., N.Y. 1989), each of which is incorporated herein by reference).

In general, an expression vector contains the expression elements necessary to achieve, for example, sustained transcription of the antisense SAPK or MEKK1 molecule or ribozyme or dominant negative mutant. In particular, an expression vector contains or encodes a promoter sequence, which can provide constitutive or, if desired, inducible expression of the encoding nucleic acid molecule, and a poly-A recognition sequence, and can contain other regulatory elements such as an enhancer, which can be tissue specific. For example, when the nucleic acid molecule contained in the vector encodes a dominant negative mutant c-jun, the vector can contain translation regulatory sequences, including a ribosome binding site. Of course, such regulatory elements can be part of the nucleic acid molecule encoding the dominant negative mutant.

A vector also can contain elements required for replication in a procaryotic or eukaryotic host system or both, as desired. Such vectors, which include plasmid vectors and viral vectors such as bacteriophage, baculovirus, retrovirus, lentivirus, poliovirus, rhinovirus, vaccinia virus, influenza virus, adenovirus, adeno-associated virus, herpes simplex virus, measles coronavirus, Sindbis virus, and semliki forest virus vectors, are well known and can be purchased from a commercial source (Promega, Madison Wis.; Stratagene, La. Jolla Calif.; GIBCO/BRL, Gaithersburg Md.) or can be constructed by one skilled in the art (see, for example, *Meth. Enzymol.*, Vol. 185, D. V. Goeddel, ed. (Academic Press, Inc., 1990); Jolly, *Canc. Gene Ther.* 1:51–64 (1994); Flotte, *J. Bioenerg. Biomemb.* 25:37–42 (1993); Kirshenbaum et al., *J. Clin. Invest* 92:381–387 (1993), which is incorporated herein by reference).

Introduction of a nucleic acid molecule encoding, for example, an antisense SAPK or a SAPK ribozyme or a dominant negative c-jun by infection with a viral vector is particularly advantageous in that it can efficiently introduce the encoding nucleic acid molecule to a cell ex vivo or in vivo. Moreover, viruses are very specialized and typically infect and propagate in specific cell types. Thus, their natural specificity can be used to target the encoding nucleic acid molecule. Viral or non-viral vectors also can be modified with specific receptors or ligands to alter target specificity through receptor mediated events.

In comparison to expressing an encoding nucleic acid molecule, an advantage of chemically synthesizing antisense nucleic acid molecules or ribozymes is that they can be stabilized against degradation by nucleases by the incorporation of a non-naturally occurring nucleoside analog or by using, for example, phosphorothioate bonds to link the nucleotides. An antisense nucleic acid molecule or ribozyme comprising a ribonucleotide containing a 2-methyl group, instead of the normal hydroxyl group, bonded to the 2'-carbon atom of ribose residues, is an example of an RNA molecule that is resistant to enzymatic and chemical degradation and, therefore, is relatively stable in vivo. Other examples of stable, chemically synthesized nucleic acid molecules include RNA containing 2'-aminopyrimidines, such RNA being 1000x more stable in human serum and urine as compared to naturally occurring RNA (see Lin et al., *Nucl. Acids Res.*, 22:5229–5234 (1994); and Jellinek et al., *Biochemistry,* 34:11363–11372 (1995), each of which is incorporated herein by reference), and RNA containing 2'-amino-2'-deoxypyrimidines or 2'-fluro-2'-deoxypyrimidines, which are less susceptible to nuclease activity (Pagratis et al., *Nature Biotechnol.,* 15:68–73 (1997), which is incorporated herein by reference).

Antisense RNA molecules or ribozymes containing 2'-0-methylpurine substitutions on the ribose residues and short phosphorothioate caps at the 3'- and 5'-ends also exhibit enhanced resistance to nucleases (Green et al., *Chem. Biol.*, 2:683–695 (1995), which is incorporated herein by reference), as do L-RNA molecules, which are a stereoisomer of naturally occurring D-RNA (Nolte et al., *Nature Biotechnol.*, 14:1116–1119 (1996), and Klobmann et al., *Nature Biotechnol.*, 14:1112–1115 (1996); each of which is incorporated herein by reference). Such RNA molecules and methods of producing them are well known and routine (see Eaton and Piekern, *Ann. Rev. Biochem.*, 64:837–863 (1995), which is incorporated herein by reference). Similarly, phosphorothioate linked oligodeoxynucleotides are nuclease resistant DNA molecules that are useful as antisense nucleic acid molecules in the present invention (Reed et al., *Cancer Res.* 50:6565–6570 (1990), which is incorporated herein by reference). Phosphorothioate-3'-hydroxypropylamine modification of the phosphodiester bond also reduces the susceptibility of a nucleic acid molecule to nuclease degradation (see Tam et al., *Nucl. Acids Res.*, 22:977–986 (1994), which is incorporated herein by reference). Of course, antisense nucleic acid molecules or ribozymes having naturally occurring nucleotides and phosphodiester bonds also can be chemically synthesized.

Chirally pure antisense molecules or ribozymes containing at least one chirally pure internucleosidyl linkage also are useful in the invention because such molecules form the appropriate angles to bind to a complementary nucleic acid molecule, thus improving the efficiency of hybridization. Such nucleic acid molecules are prepared using known methods (see, for example, Lesnikowski et al., *Nucl. Acids Res.* 18:2109–2115 (1990); Stec et al., *Nucl. Acids Res.* 19:5883–5888 (1991), each of which is incorporated herein by reference).

Methylphosphonate antisense molecules or ribozymes also can be useful (see Lee et al., *Biochemistry* 27:3197–3203 (1988); and Miller et al., *Biochemistry* 25:5092–5097 (1986); PCT applications WO 92/07864 and WO/07882, each of which is incorporated herein by reference), as are antisense molecules or ribozymes that are nucleoside/non-nucleoside polymers or chimeric oligonucleotides that are composite RNA, DNA analogs (Inoue et al., *FEBS Lett.* 2115:327 (1987)), which can have chimeric backbones. Antisense nucleic acid molecules or ribozymes having chimeric backbone include those having mixed phosphate backbones, including nucleoside sequences that are capable of activating RNase H, which allows site directed cleavage of an RNA molecule (see U.S. Pat. No. 5,149,797, which is incorporated herein by reference). Antisense nucleic acid molecules or ribozymes having chimeric backbones also include those having a mixture of internucleosidyl linkages and those having a neutral backbone, for example, methylphosphonate nucleic acid molecules. Such nucleic acid molecules can have a longer half-life in vivo, since the neutral structure reduces the rate of nuclease digestion. The addition of a cleaving or cross-linking moiety also can be useful and can promote inactivation of target polynucleotide sequences. Conjugation partners also can be introduced into the antisense molecules or ribozymes by incorporating modified nucleosides or nucleoside analogs using enzymatic or chemical modification of the nucleic acid molecule, for example, by the use of non-nucleotide linker groups.

A chemically synthesized antisense nucleic acid molecule or ribozyme can be introduced into a cell by any of a variety of methods known in the art (Sambrook et al., supra, 1989, and in Ausubel et al., *Current Protocols in Molecular Biology*, John Wiley and Sons, Baltimore, Md. (1994), which is incorporated herein by reference), including, for example, transfection, lipofection, microinjection, electroporation or the use of liposomes. In addition, it is recognized that naked nucleic acid molecules are taken up by cells in vivo and, therefore, that the antisense nucleic acid molecule or ribozyme of the invention simply can be administered directly to the region containing the cancer cells, where appropriate. In particular, antisense nucleic acid molecules or ribozymes can be introduced into a cell using methods that do not require the initial introduction of an encoding nucleic acid molecule into a vector. For example, a nucleic acid molecule encoding an antisense SAPK isozyme or MEKK1 can be introduced into a cell using a cationic liposomes, which also can be modified with specific receptors or ligands as described above (Morishita et al., *J. Clin. Invest.*, 91:2580–2585 (1993), which is incorporated herein by reference; see, also, Nabel et al., supra, 1993)). In addition, a nucleic acid molecule can be introduced into a cell using adenovirus-polylysine DNA complexes (see, for example, Michael et al., *J. Biol. Chem.*, 268:6866–6869 (1993), which is incorporated herein by reference).

Specific portions of a SAPK nucleic acid molecule or a MEKK1 nucleic acid molecule to be targeted by the antisense nucleic acid or the ribozyme ("target nucleic acid") can be selected based on the sequence of the target nucleic acid (see GenBank Accession numbers, as disclosed above). In addition, based on comparisons of the disclosed MEKK1 and SAPK nucleic acid sequences, an antisense nucleic acid molecule or ribozyme can be designed such that it is specific only for MEKK1 or only for a single SAPK isozyme or can be more promiscuous, inhibiting the expression of MEKK1 and a SAPK or various SAPK isozymes or all SAPK isozymes.

Antisense nucleic acid molecules useful in the invention can be selected using well known and routine methods. For example, a panel of antisense nucleic acid molecules that are complementary to various 5'-untranslated, coding and 3'-untranslated regions of the target nucleic acid molecule, for example, SAPK1α1 or MEKK1, can be prepared and can be examined using in vitro assays to select those antisense molecules that have the desired specificity (see, for example, Monia et al., *Nature Med.* 2:668–674 (1996); Dean et al., *Cancer Res.* 56:3499–3507 (1996), each of which is incorporated herein by reference). It is recognized that the ability of an antisense nucleic acid molecule (or a ribozyme) to hybridize to the target nucleic acid depends, for example, on the degree of complementarity shared between the sequences, the GC content of the hybridizing molecules, and the length of the antisense nucleic acid molecule or complementary portion of the ribozyme. In particular, specificity of hybridization can be such that an antisense SAPK or a ribozyme binds to one or a selected few SAPK isozymes, but not to others (see, for example, Dean et al., supra, 1996).

In view of the above disclosure relating to the selection of target sequences in a SAPK or MEKK1, the skilled artisan would recognize that ribozymes also can be used to inhibit the activity of a SAPK or MEKK1. Ribozymes comprise two ribonucleic acid sequences, which are complementary to a target nucleic acid sequence, flanking an RNA sequence that can cleave a specific RNA sequence (Cech, *J. Amer. Med. Assoc.*, 260:303b (1988)). Two basic types of ribozymes, "tetrahymena-type" (Hasselhoff, *Nature* 334:585 (1988)) and "hammerhead-type," are known. Tetrahymena-type ribozymes specifically recognize sequences that are four bases in length, while hammerhead ribozymes recognize sequences that are 11 to 18 bases in length. The location of specific ribozyme target sequences can be identified by examination of the SAPK and MEKK1 sequences disclosed above and ribozymes can be constructed containing the ribozyme sequence flanked by additional target sequences such that the ribozyme specifically hybridizes to the target sequence. Ribozymes can be constructed and introduced into cells as disclosed above.

Since cells, including normal cells and cancer cells can express one or more specific SAPK isozymes, the identification of the specific isozymes expressed provides specific targets for which the antisense nucleic acid molecules or ribozymes are designed. The use of antisense nucleic acid molecules or ribozymes that target specific SAPK isozymes also can provide a means to further spare normal tissue from the effects of the cancer therapeutic modality, since, where normal cells that are particularly sensitive to the cancer therapeutic modality express a SAPK that is different from at least one SAPK expressed in the cancer cells, the antisense SAPK nucleic acid molecule can be designed to inhibit the expression of the cancer cell SAPK but not the normal cell SAPK. For example, where the cancer therapeutic modality is radiotherapy, the SAPK isozyme expressed in normal cells that are within the radiation field can be identified and, where the SAPK isozyme in the cancer cells is different, the antisense SAPK nucleic acid molecule can be designed to inhibit expression of the cancer cell SAPK isozyme, but not the normal cell SAPK isozyme. In this regard, it is noted that cancer therapeutic modalities generally are toxic to rapidly renewing tissues, including blood cells and epithelial cells. The identification of SAPK isozymes that generally are expressed, or not expressed in such tissues, therefore, can be informative to practicing the methods with most cancer therapeutic modalities.

Methods for identifying which specific SAPK isozymes are expressed in cancer cells and normal cells are routine and can utilize, for example, nucleic acid hybridization using SAPK isozyme specific probes. For example, northern blot or dot blot analysis provides rapid and simple assays for determining the specific SAPK isozymes expressed in a cell. Probes that are selective for one or more SAPK isozymes can be obtained by performing computerized searches of the nucleic acid sequences encoding the various isozymes (see GenBank Accession numbers, above) and identifying unique sequences that will specifically hybridize to the desired nucleic acid molecule under stringent hybridization conditions.

As disclosed herein, a dominant negative mutant of c-jun such as dn-jun, which lacks serine-63 and serine-73 and cannot be phosphorylated by SAPK, provides an additional example of a SAPK inhibitory agent that can inhibit SAPK activity and can increase the sensitivity of various cancer cells, including glioblastoma cells, prostate cancer cells and breast cancer cells, to a cancer therapeutic modality, cis-platinum (see Examples I and II). For example, the expression of a dn-jun, which contained alanine-63 and alanine-73 substitutions, in glioblastoma cells inhibited phosphorylation-dependent activation of transcription, but did not have a significant effect on SAPK activity, suggesting that dn-jun does not strongly bind to or competitively inhibit the SAPK enzyme, but competes with normal c-jun for binding to a Fos family member or to ATF2. These results indicate that a dominant negative c-jun inhibits the ability of SAPK to promote phosphorylation-dependent activation of transcription. In particular, expression of dn-jun in the glioblastoma cells sensitized the cells to cis-platinum and decreased the concentration of cis-platinum required to kill 50% of the cells (IC-50) seven-fold (Example I). In addition, expression of a different dominant negative c-jun mutant, Tam-67, sensitized prostate cancer cells to cis-platinum. Thus, dominant negative c-jun mutants are useful generally for sensitizing various cancer cells to a cancer therapeutic modality.

A dominant negative c-jun can be any of various c-jun mutants, provided the mutation results in an inability of phosphorylation of serine-63 and serine-73. Thus, a dn-jun can contain amino acid substitutions such as the alanine-63 and alanine-73 substitutions in the dn-jun disclosed herein (see Smeal et al., *Nature* 354:494–496 (1991), which is incorporated herein by reference). In addition, a dn-jun can be a deletion mutant of c-jun, such as the Tam-67 c-jun mutant, which contains a deletion of amino acids 3 to 122 (Lenczowski et al, *Mol. Cell. Biol.* 17:170–181 (1997); Brown et al., *Oncogene* 8:877–886 (1993); Alani et al., *Mol. Cell. Biol.* 11:6286–6295 (1991), each of which is incorporated herein by reference). Furthermore, the SAPK pathway and, therefore, SAPK activity can be inhibited by expressing, instead of a dominant negative c-jun, a dominant negative ATF2 (van Dam et al., *EMBO J.* 14:1798–1811 (1995), which is incorporated herein by reference) or a dominant negative SAPK (see, for example, Gupta et al., *Science* 267:389–391 (1995); Chen et al., *J. Biol. Chem.* 271:31929–31936 (1996); Clark et al., *J. Biol. Chem.* 272:1677–1681 (1997), each of which is incorporated herein by reference). Methods for producing such dominant negative mutants are routine in view of the ready availability of the nucleic acid sequences encoding the relevant proteins and in view of the cited references, which generally describe the regions of the proteins, such as SAPK and c-jun, that are required for SAPK activity.

A small molecule also can act as a SAPK inhibitory agent, for example, by inhibiting the activity of a kinase in the pathway or by interfering with a step of the pathway. For example, a small molecule can alter the association of two proteins such as SAPK kinase with a SAPK in the SAPK pathway, thus preventing phosphorylation of the SAPK and terminating the SAPK pathway. Small molecules that can inhibit SAPK activity generally are organic molecules, including peptides and drugs, which contain a reactive group that can be varied. Thus, libraries of peptides can be prepared, wherein each amino acid is a reactive group that can be varied (see, for example, U.S. Pat. No. 5,264,563, issued Nov. 23, 1993; U.S. Pat. No. 5,223,409, issued Jun. 29, 1993, each of which is incorporated herein by reference). For example, the sequence comprising amino acids 33 to 79 of c-Jun binds a cleft associated with the active site of SAPK (Derijard et al., supra, 1994; Gupta, supra, 1996). Accordingly, a library of diverse peptides based on this sequence of c-jun can be prepared and the peptides can be screened to identify those that alter SAPK activity, particularly the ability of a SAPK to phosphorylate c-jun on serine-63 and serine-73. In addition, libraries of small organic molecules such as drugs can be prepared by combinatorial organic synthesis such that the molecules that share a common structure but vary in a reactive group are produced (see, for example, Gordon et al., *J. Med. Chem.* 37:1385–1401 (1994)). Such libraries of molecules can be synthesized using known methods and are commercially available.

It should be recognized that a library of small molecules can be screened to identify those agents useful for inhibiting a SAPK pathway. For example, the library of molecules can be screened against particular cancer cells and the ability of the molecules to increase or decrease the activity of a SAPK in the cells can be determined using methods as disclosed herein. Those molecules that inhibit SAPK activity are identified as agents that can increase the sensitivity of a cancer cell to a cancer therapeutic modality and, therefore, are useful in the invention. It should further be recognized that molecules that increase SAPK activity also will be identified by such screening methods and that such agents are particularly useful, for example, for protecting normal cells from a cancer therapeutic modality.

In addition, methods of rational drug design have been developed and can be used to prepare small molecules useful for inhibiting a SAPK pathway and SAPK activity (Jackson, Sem. Oncol. 24:264–172 (1997); Webber et al., J. Med. Chem. 39:5072–5082 (1996); Hopkins et al., J. Med. Chem. 39:1589–1600 (1996), each of which is incorporated herein by reference). For example, the crystal structure of a SAPK or MEKK1 can be determined to a resolution of about 3 angstroms and the active site of the kinase can be defined with respect to positive and negative charges. A small molecule presenting the appropriate opposite charges in the appropriate orientation and configuration then can be designed. If desired, appropriate hydrophobic groups can be incorporated into the molecule. Computer programs are available for determining, for example, correct chemical bond lengths and angles and steric hindrance and attraction forces. For example, the choice of a small molecule can be based on a derivative of ATP, which is bound by SAPK and MEKK1.

Since a SAPK inhibitory agent such as a small organic molecule, an antisense SAPK or MEKK1 nucleic acid molecule, a SAPK or MEKK1 specific ribozyme, or a dominant negative mutant inhibitor of activity of a SAPK generally is used to sensitize cancer cells, the agent can be formulated into a composition that is convenient for contacting the agent with the cancer cells. Such contacting can be to cells in culture or can be to an individual.

As used herein, the term "SAPK inhibitory agent" is used broadly to mean a small organic molecule or a DNA, RNA or polypeptide that inhibits a SAPK pathway. Thus, as disclosed herein, a SAPK inhibitory agent can be a small molecule, i.e., a drug; an antisense SAPK or MEKK1 molecule; a SAPK or MEKK1 specific ribozyme; a nucleic acid molecule encoding such an antisense molecule or ribozyme; or a nucleic acid encoding a dominant negative mutant such as a dominant negative c-jun mutant or the encoded polypeptide. Furthermore, a nucleic acid molecule agent can be in various forms, including naked DNA or RNA, either alone or in a vector, and, when part of a vector, can be, for example, a naked vector, or a vector encapsulated in a liposome or microemulsion or the like, or a vector contained within or associated with a virus particle. The term "SAPK inhibitory agent" encompasses these forms and others known in the art.

A SAPK inhibitory agent can be formulated as a pharmaceutical composition, which contains the agent and a pharmaceutically acceptable carrier. Pharmaceutically acceptable carriers are well known in the art and include aqueous solutions such as water, physiologically buffered saline or other solvents or vehicles such as glycols, glycerol, oils such as olive oil or injectable organic esters.

A pharmaceutically acceptable carrier can contain physiologically acceptable compounds that act, for example, to stabilize the or increase the absorption of the SAPK inhibitory agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the SAPK inhibitory agent and on the particular physicochemical characteristics of the specific agent, i.e., whether it is DNA or RNA or a polypeptide and, where DNA or RNA, whether the molecule contains naturally occurring nucleotides and phosphodiester bonds or analogs of such nucleotides and bonds.

A SAPK inhibitory agent can be administered to an individual by various routes including, for example, orally or parenterally, such as intravenously, intramuscularly, subcutaneously, intraorbitally, intracapsularly, intraperitoneally, intrarectally intracisternally or by passive or facilitated absorption through the skin using, for example, a skin patch or transdermal iontophoresis, respectively. Furthermore, a composition comprising a SAPK inhibitory agent can be administered by injection, intubation, orally or topically, the latter of which can be passive, for example, by direct application of an ointment or powder, or active, for example, using a nasal spray or inhalant. A SAPK inhibitory agent also can be administered as a topical spray or an inhalant, in which case one component of the composition is an appropriate propellant.

The pharmaceutical composition also can be incorporated, if desired, into oil-in-water emulsions, microemulsions, micelles, mixed micelles, liposomes, microspheres or other polymer matrices (Gregoriadis, *Liposome Technology*, Vol. 1 (CRC Press, Boca Raton, Fla. 1984); Fraley, et al., *Trends Biochem. Sci.*, 6:77 (1981), each of which is incorporated herein by reference) Liposomes, for example, which consist of phospholipids or other lipids, are nontoxic, physiologically acceptable and metabolizable carriers that are relatively simple to make and administer. In addition, liposomes are particularly useful because they can 1) encapsulate a SAPK inhibitory agent with high efficiency while not compromising the biological activity of the agent; 2) preferentially and substantially bind to a target cell; and 3) deliver the aqueous contents of the vesicle into the target cell with high efficiency (see Mannino et al., *Biotechniques* 6:682 (1988)).

Targeting of liposomes to a cancer in an individual can be passive or active. Passive targeting, for example, utilizes the tendency of liposomes to accumulate in cells of the reticuloendothelial system (RES) and in organs such as the liver, which contain sinusoidal capillaries. Active targeting, in comparison, involves alteration of the liposome by coupling a specific ligand such as a monoclonal antibody, a sugar, a glycolipid or a protein such as a ligand for a receptor expressed by the target cells. Either method of targeting can be selected, based on the type and location of the cancer. For example, passive targeting can be an effective means for delivering a SAPK inhibitory agent to a liver cancer due to the concentration of RES cells in the liver and the sinusoidal nature of the circulatory system in the liver.

In addition, it is recognized that tumors, as they increase in size, develop necrotic centers and that blood vessels in the region of the necrotic centers become "incompetent" or "leaky" (see Maragoudakis et al., "Angiogenesis: Molecular biology, clinical aspects" (Plenum Press 1994); Walmsley et al., *Scan. Microsc.* 1:823–830 (1987); Zama et al., *J. Cancer Res. Clin. Oncol.* 117:396–402 (1991)). Thus, intravenous or intra-arterial administration of a SAPK inhibitory agent, particularly into a blood vessel that carries blood to the tumor, preferentially should permit accumulation of the agent in the tumor.

In order to sensitize cancer cells to a cancer therapeutic modality, the SAPK inhibitory agent is administered in an amount that can inhibit SAPK activity or expression. In general, the amount of an antisense molecule or a nucleic acid encoding a dominant negative inhibitor of the SAPK pathway administered to an individual and the frequency of administrations is determined, initially, in Phase I and Phase II clinical trials. For example, antisense SAPK nucleic acid molecules can be administered in graded steps of increasing dose in the range of 1 ng/kg to 10 mg/kg in Phase I trials in order to determine a dose useful for inhibiting SAPK activity or expression without producing unacceptable toxicity to the individual (see Dean et al., supra, 1996). In additional cohorts, the graded series can be combined with a conventional cancer therapeutic modality in order to establish combination doses useful for inhibiting SAPK activity or expression without toxicity to the individual. In addition, where the antisense nucleic acid molecule is expressed, for example, from a viral vector, or where a dominant negative mutant is expressed from a viral vector, Phase I trials can be performed using $10^6$ to $10^{10}$ colony forming units. The viral vector is purified to a concentration ranging from 0.25% to 25%, preferably about 5% to 20% before formulation. After formulation, a dose of about 1 pg to 100 ng viral vector is contained in approximately 0.1 ml to 1.0 ml of the pharmaceutical composition.

Where a SAPK inhibitory agent is administered to an individual, the total dose can be administered as a single dose, either as a bolus or by infusion over a relatively short period of time, or can be administered using a fractionated treatment protocol, in which the multiple doses are administered over a more prolonged period of time. The skilled artisan would know that the concentration of a SAPK inhibitory agent required to inhibit SAPK activity in a subject depends on many factors including the age and general health of the subject as well as the route of administration and the number of treatments to be administered. In view of these factors, the skilled artisan would adjust the particular dose as necessary. For example, where the SAPK inhibitory agent is to be administered in order to sensitize cancer cells to a cancer therapeutic modality, the SAPK inhibitory agent can be administered prior to or in concert with the cancer therapeutic modality. Methods for administering conventional cancer therapeutic modalities are well known in the art.

Although the invention is particularly useful for increasing the sensitivity of cancer cells to a cancer therapeutic modality, the invention also can be practiced on essentially any type of cell where the goal is to increase the genotoxic effect of a cancer therapeutic modality as defined herein. For example, a method of the invention can be practiced against immunoeffector cells so as to sensitize the cells to an immunosuppressive agent, which is used for treating a patient prior to transplantation or for treating a patient with an auto-immune disease. Furthermore, a SAPK inhibitory agent as disclosed herein can be used to sensitize essentially any type of cancer cell, including carcinoma cells and sarcoma cells, as well as cancer cells in a central nervous tumor, a melanoma, a leukemia, a lymphoma, ovarian cancer, bone cancer, lung cancer, colorectal cancer, hepatocellular carcinoma, glioblastoma, prostate cancer, breast cancer, bladder cancer, kidney cancer, pancreatic cancer, gastric cancer, biliary cancer, urogenital cancer, and head and neck cancer. The usefulness of the methods of the invention against such a variety of cancers or other population of cells where it is desired that the cells be sensitized to a genotoxic drug is apparent in view of the conservation of the SAPK pathway in all mammalian cells. Accordingly, the present invention provides methods of increasing the sensitivity of a cell to a genotoxic drug by inhibiting the activity of a SAPK in the cell, for example, increasing the sensitivity of cancer cells to a cancer therapeutic modality.

The invention further provides methods to reduce the severity of a pathology in an individual, wherein the pathology is due to a population of cells, by administering a SAPK inhibitory agent to the individual and treating the individual with a genotoxic drug. For example, the invention provides a method of reducing the severity of a cancer in a patient, comprising administering to the patient a SAPK inhibitory agent and treating the patient with a cancer therapeutic modality. As used herein, the term "reduce the severity," when used in reference to a pathology such as cancer, means that the clinical symptoms or signs of the disease are lessened.

A method of the invention provides a means, for example, to reduce the severity of a cancer by increasing the sensitivity of the cancer cells to a cancer therapeutic agent. For example, expression of a dominant negative c-jun mutant in various tumor cells, including glioblastoma cells, breast cancer cells (Example I) and prostate cancer cells (Example II), reduced the dose of cis-platinum required to kill 50% of the cells (IC-50), as compared to the dose required to kill cells not expressing the dominant negative c-jun. Thus, a method of the invention allows the administration of a lower dose of a conventional cancer therapeutic modality such as a chemotherapeutic agent or radiation than would be required if SAPK activity was not inhibited.

This method also improves the efficacy of a therapy that leads to an increase in the expression of cytokines that are known to activate c-jun, particularly in tumor cells. Such cytokines including, but not limited to, interleukins (IL) such as IL-2, IL-6, IL-7 and IL-12, the tumor necrosis factors, interferons, and various growth factors, including EGF, PDGF and TGF-α, GM-CSF and G-CSF (see, for example, Kyriakis et al., *Nature* 369:156–160 (1994)). In addition, a method of the invention improves a therapy that has, as an effect, the release of inflammatory intermediates that activate SAPK in tumor cells. Furthermore, introduction of antisense oligonucleotides or expression vectors that encode them makes tumor cells better targets for the immune system by restoring the apoptotic pathways required for killing by cytotoxic immune T cells, lymphokine activated killer cells, natural killer cells, macrophages, monocytes, and granulocytes.

The following examples are intended to illustrate but not limit the present invention.

EXAMPLE I

DOMINANT NEGATIVE C-JUN SENSITIZES GLIOBLASTOMA CELLS TO KILLING BY CIS-PLATINUM

This example demonstrates that inhibition of SAPK activity by expression of a dominant negative c-jun (dn-jun) in glioblastoma cells sensitizes the cells to killing by cis-platinum.

T98G glioblastoma cells were maintained in Dulbecco's modified minimal medium containing 5% fetal calf serum. SAPK (JNK) assays were performed as described by Hibi et al. (supra, 1993). c-jun and dn-jun expression were quantitated using the methods and antibodies described by Grover-Bardwick et al. (*Carcinogenesis* 15:1667–1674 (1994), which is incorporated herein by reference).

Cisplatin, but not transplatin, forms covalent crosslinks between adjacent guanine or guanine-adenine residues.

Incubation of T98G cells with 250, 500 or 1000 μM cisplatin for 1 hr produced a dose-dependent increase (up to 10-fold) in SAPK (JNK) activity, whereas no effect was observed with transplatin. As a control, UV-C irradiation was performed and similarly produced a dose-dependent increase in SAPK activity. Similar results were observed using two human non-small cell lung carcinoma cell lines (A549 and M103). These results indicate that cisplatin, but not transplatin, increase SAPK activity in various cancer cell lines.

T98G cells were stably transfected with a cDNA encoding the dn-jun (Smeal et al., supra, 1991; Smeal et al., supra, 1992) and clonal lines were obtained. Expression of dn-jun had no effect on basal AP-1 activity or on the enzyme activity of SAPK. In contrast, dn-jun expression inhibited phosphorylation-dependent activation of transcription.

Cell viability was determined using the MTS method (Promega Corp.; Madison Wis.), measuring the A590 of the formazan product 1 hr after adding the MTS (Gjerset et al., *Mol. Carcin.* 14:275–285 (1995), which is incorporated herein by reference). Cells were seeded into 96 well plates. After 24 hr, various concentrations of cisplatin or transplatin was added and incubation was continued for 1 hr. Medium was then removed and replaced with fresh medium and cell viability was determined 5 days later. Experiments were performed in quadruplicate; cell viability is expressed as the ratio of the viable cells following treatment to viable untreated cells.

The IC-50 for cisplatin was determined using the T98G cells that express dn-jun, control T98G cells and T98G cells stably transfected with the corresponding empty vector. No significant difference was observed between the control (untransfected) T98G cells or the vector transfected T98G cells (IC-50=147 μM and 154 AM, respectively). In comparison, expression of dn-jun in T98G cells decreased the IC-50 to 21 μM, which represents a 7-fold increase in sensitivity. Furthermore, when various clonal dn-jun transfected T98G cells were examined, the IC-50 correlated to the steady-state level of dn-jun expressed in the cells ($r_{Pearson}$=0.98) In comparison, increased expression of c-jun in T98G cells somewhat increased the viability of cells to cisplatin exposure, suggesting that an increased amount of the SAPK substrate in cells augments their viability In other experiments, U87 human glioblastoma cells and MCF-7 breast cancer cells were stably transfected with the vector expressing dn-jun and clonal lines were isolated. U87 cells expressing dn-jun showed a 2.5-fold increased sensitivity to cisplatin as compared to parental U87 cells, and MCF-7 cells expressing dn-jun showed a 3-fold increased sensitivity as compared to the parental cells. These results indicate that expression of dn-jun in various cancer cell lines sensitizes the cells to cisplatin.

The PCR-stop assay was used to quantitate cisplatin-DNA adduct formation and subsequent repair (Horton et al., *Nucl. Acids. Res.* 23:3810–3815 (1995), which is incorporated herein by reference). The assay is based on the observation that the efficiency of amplification of cisplatin-treated DNA is inversely proportional to the degree of platination. Cells were treated with various concentrations of cis-platinum (cisplatin) or transplatin for 1.25 hr, then genomic DNA was isolated immediately or 6 hr later. DNA was amplified quantitatively to produce a 2.7 kb product of the hypoxanthine phosphoribosyl transferase (HPRT) gene and a 0.15 kb nested fragment of the HPRT gene using $^{32}$P-end labeled primers: 5'-TGGGATTACACGTGTGAACCAACC-3'(5' primer; SEQ ID NO: 3) and 5'-GATCCACAGTCTGCCTGAGTCACT-3' (3' primer; SEQ ID NO: 4), for the 2.7 kb product; 5'-CCTAGAAAGCACATGGAGAGCTAG-3'(5' nested primer; SEQ ID NO: 5) and the above 3' primer (SEQ ID NO: 4) for the 0.15 kb product. The 0.15 kb product contains undetectable levels of DNA damage under the present conditions and serves as an internal PCR control and as the basis for normalization of the amount of amplification of the 2.7 kb product. The number of lesions per 2.7 kb product was calculated as 1 minus (cpm damaged DNA/cpm undamaged DNA).

DNA isolated for T98G cells immediately after a 1 hr treatment with 0, 100 or 200 μM cisplatin showed increasing levels of DNA damage. However, if a 6 hr recovery period was allowed prior to isolating the DNA, damage was markedly and significantly (p=0.003) reduced. As a control, 2-aminobenzidine (ABZ), which inhibits DNA repair by inhibiting ADP-ribosylation, was added with cisplatin. Following the 6 hr recovery period, no repair was observed in the ABZ treated cells and the level of damage was substantially increased. In experiments performed using T98G cells expressing dn-jun, DNA damage remained completely unrepaired, following the 6 hr "recovery" period, in cells treated with either 100 μM or 200 μM cisplatin (p>0.53). These results indicate that dn-jun inhibits DNA repair in cisplatin treated glioblastoma cells.

EXAMPLE II

DOMINANT NEGATIVE C-JUN SENSITIZES PROSTATE CARCINOMA CELLS TO KILLING BY CIS-PLATINUM

This example demonstrates that expression of a dn-jun in prostate carcinoma cells sensitizes the cells to killing by cis-platinum, thus confirming the general applicability of the claimed invention.

PC3 prostate carcinoma cells were genetically modified to express dn-jun or a second dominant negative c-jun, Tam-67, both of which were under control of the metallothionein promoter (Brown et al., *Oncogene* 9:791–799 (1994), which is incorporated herein by reference). Viability studies showed an IC-50 of 109 μM for the control PC3 cells and 154 AM for PC3 cells transfected with the corresponding empty vector. In comparison, PC3 cells expressing dn-jun had an IC-50 of 18 μM, representing an increased sensitivity of greater than 7-fold and greater than 9-fold above the control and vector control cells, respectively. Similarly, expression of Tam-67 strongly enhanced the sensitivity of the PC3 cells to cisplatin. These results demonstrate that various dominant negative c-jun mutants can sensitize cancer cells to cisplatin and confirm the general applicability of the claimed invention.

Although the invention has been described with reference to the examples provided above, it should be understood that various modifications can be made without departing from the spirit of the invention. Accordingly, the invention is limited only by the claims.

I claim:

1. A method of increasing the sensitivity of glioblastoma, non-small cell lung, breast or prostate cancer cells to a cancer therapy, comprising contacting the cancer cells with a vector expressing at least one stress activated protein kinase (SAPK) pathway inhibitor wherein said SAPK pathway inhibitor is a dominant negative c-jun mutant.

2. A method of increasing the sensitivity of glioblastoma, non-small cell lung, breast, or prostate cancer cells to a cancer therapy in a patient suffering from glioblastoma, non-small cell lung, breast, or prostate cancer, comprising administering a vector expressing at least one SAPK pathway inhibitor to the cells wherein said pathway inhibitor is a dominant negative c-jun mutant and treating the patient with a cancer therapy.

3. A method according to claim 1 wherein said dominant negative c-jun mutant is dn-jun(ala63,ala73).

4. A method according to claim 1 wherein said dominant negative c-jun mutant is Tam-67.

5. A method according to claim 1 wherein said dominant negative c-jun mutant is dn-ATF2 mutant.

6. A method according to claim 2, wherein said dominant negative c-jun mutant is dn-jun(ala 63,ala73).

7. A method according to claim 2, wherein said dominant negative c-jun mutant is Tam-67.

8. A method according to claim 2, wherein said dominant negative c-jun mutant is dn-ATF2 mutant.

* * * * *